United States Patent [19]

Paxson

[11] 4,450,288

[45] * May 22, 1984

[54] BUTENYL ACETATE PRODUCTION

[75] Inventor: Timm E. Paxson, Houston, Tex.

[73] Assignee: Shell Oil Company, Houston, Tex.

[ * ] Notice: The portion of the term of this patent subsequent to May 22, 2001 has been disclaimed.

[21] Appl. No.: 380,639

[22] Filed: May 21, 1982

[51] Int. Cl.$^3$ ..................... C07C 67/04; C07C 69/145
[52] U.S. Cl. .................................. 560/241; 560/261; 568/398
[58] Field of Search ............................. 560/241, 261

[56] References Cited

U.S. PATENT DOCUMENTS 2,746,938  5/1956  Ehm et al. ............................ 560/263
4,323,698  4/1982  Haag et al. .......................... 560/241

FOREIGN PATENT DOCUMENTS 49-24476  6/1974  Japan .................................. 560/241

Primary Examiner—Vivian Garner

[57] ABSTRACT

A process for producing butenyl acetate which comprises reacting butadiene and acetic acid in the presence of a catalyst comprising a sulfonic acid ion exchange resin modified with an alkyl pyridinium salt.

4 Claims, No Drawings

BUTENYL ACETATE PRODUCTION

FIELD OF THE INVENTION

This invention relates to a process for producing primary and secondary butenyl acetates by reacting butadiene and acetic acid in the presence of a modified sulfonic acid ion exchange resin catalyst.

BACKGROUND OF THE INVENTION

Butenyl acetates are very useful chemical intermediates. For example, methyl ethyl ketone can readily be synthesized from secondary butenyl acetate and normal butyl alcohol can readily be synthesized from normal butenyl acetate and the acetate moiety recycled as acetic acid. Butadiene and acetic acids are relatively inexpensive and readily available feedstocks. A process that would upgrade butadiene to a higher value product would have significant economic advantage.

Addition reactions involving butadiene, for example, additions of water or alcohols, are known to be catalyzed by acid catalysts such as, for example, sulfuric acid or sulfonic acid ion exchange resins. The instant process utilizes a modified sulfonic acid ion exchange resin to provide for high selectivities to the primary and secondary butenyl acetates.

SUMMARY OF THE INVENTION

This invention relates to a process for producing butenyl acetates which comprises reacting butadiene and acetic acid in the presence of a catalyst comprising styrene-divinylbenzenesulfonic acid ion exchange resin wherein from about 2 to about 20% of the sulfonic acid moieties of the resin are exchanged with an alkyl pyridinium salt. The use of the modified ion exchange resins of the instant invention in the present process provides for a higher selectivity to the butenyl acetates and lower selectivity to the octadienyl acetates and higher telomeric acetates than the use of unmodified resins.

DESCRIPTION OF THE PREFERRED EMBODIMENTS

The ion exchange resins utilized to prepare the catalysts of the instant invention are the strongly acidic, polystyrene-based cation exchange resins. These materials are based on the styrene monomer repeating unit with a controlled amount of divinylbenzene incorporated as a cross-linking agent which lends rigidity to the polymer matrix. Sulfonation, as a rule, is carried out on a finished polymer; such that typically, over 70% of the available benzene rings are mono substituted with the $-SO_3H$ moiety during sulfonation. Very little disulfonation occurs. Historically, these sulfonated resins have found extensive use as synthetic ion exchange materials, but recently they are finding applications as solid acid catalysts. The content of divinylbenzene in these resins has a significance on the structure of the resins. Depending on the amount of divinylbenzene, the resins are divided into two major groups, the microreticular or gellular resins and the macroreticular resins. The boundary condition is generally considered to be about 12% in divinylbenzene content; above this content the resin is considered to be one of the macroreticular class which is characterized by a more rigid structure and a large matrix resistance to swelling in aqueous solutions or collapse in organic solutions. These macroreticular resins are the preferred resins of use to prepare the catalysts for the instant invention. Typical commercially available examples of suitable ion exchange resins are the AG-50W series of Bio-Rad, the Dowex® 50W series of Dow Chemical Company, the Duolite® C-20 series of Diamond Shamrock, the Amberlite® IR-120 series and the Amberlist® 15H series of Rohm & Haas Company and the Dowex MSC-1H material of Dow Chemical Company and the XN 1010 material of Rohm & Haas.

The alkyl pyridinium salts have the general formula $(C_5H_5N+R)_m A_n^q$ where R is alkyl with a carbon number from 1 to about 20, A is an anionic moiety with charge q, and n and m are integers sufficient to balance out the charges at the anion and the pyridinium moiety. In addition to the alkyl group R, the pyridinium moiety may be unsubstituted or substituted with other substituents such as alkyl or halo, i.e., it may be derived from pyridine or substituted pyridines. Substituted pyridines useful for preparing the pyridinium salt include, among others, picolines, lutidines, collidines, conyrines, parvulines, coridines, rubidine, viridine, 2-chloro-pyridine, 2-chloro-5-methyl-pyridine, 2,3,5,6-tetrachloro-pyrine and the like.

The anionic moiety of the pyridinium salt is either the hydroxide or the anion of a strong or weak acid such as, for example, iodide, bromide, chloride, nitrate, sulfate, bisulfate, thiosulfate, acetate, oxalate, and other carboxylates, and the like.

Illustrative examples of alkyl pyridinium salts useful in the instant invention are given as follows:
methyl 3-methylpyridinium iodide
n-propyl 2-ethylpyridinium bisulfate
pentyl pyridinium acetate
octyl pyridinium sulfate
dodecyl pyridinium hydroxide
pentyl 2-methylpyridinium chloride
hexyl 3-methyl-5-chloropyridinium acetate To prepare the catalysts of the instant invention, the ion exchange resin is put into the hydrogen form if it is not already in that form, and then contacted with a solution of the appropriate pyridinium salt. A very satisfactory solvent for the pyridinium salt is an aqueous solution of acetic acid. The modified resins are thus prepared by exchanging from about 2% to about 20%, preferably from about 3% to about 10%, of the sulfonic acid moieties of the ion exchange resin with the alkyl pyridinium salt.

The modified ion exchange resin catalysts of this invention are used in typical fashion, for example, in packed beds, in batch reactors, or in fluidized beds. Reaction temperatures typically range from about 0° to about 150° C., preferably from about 25° to about 125° C. and more preferably from about 40° to about 100° C. The reaction product is subjected to standard separation processes and product butylene acetate is separated from unreacted butadiene and acetic acid. Suitable inert solvents may also be utilized in the process of the instant invention, such as, for example, aliphatic compounds such as hexane, dodecane, etc., aromatic compounds such as benzene, xylene, toluene and other compounds not containing olefinically unsaturated bonds. The reactants may be fed directly to the reactor, or the butadiene, for example, may be predissolved in the acetic acid and the resulting solution then fed directly to the reactor. Reaction pressures are not critical, and they may be atmospheric, super- or subatmospheric pressures, pressures ranging from about 1 to about 5 atmospheres being typically utilized.

The preparation of the catalysts used in the instant process and the utilization of these catalysts will be further described by the following illustrative embodiments which are provided for illustration and not to be construed as limiting the invention.

ILLUSTRATIVE EMBODIMENTS

Catalyst Preparation

A general preparative technique is as follows: about 300 millimeters of appropriate resin beads are placed in a 600-milliliter sintered glass (coarse) filter funnel and gravity washed with 3 liters of a 1.0 N aqueous HCl solution in order to convert the resin to the acid form. This is followed by an aqueous wash of 4 to 5 liters of deionized water. The resin is then air dried by vacuum application to the filter funnel and then vacuum oven dried at about 50°–70° C. for about 24–48 hours with a slow stream of nitrogen flowing through the oven. Materials are stored in sealed glass bottles prior to use. The modification of the resins is accomplished by a treatment of the resins with an acetic acid solution of the alkyl pyridinium salt. The desired amount of modifier is dissolved in acetic acid and continuously circulated through a bed of the resin for about 24 hours. At the end of this time period, the resin is collected in a sintered glass funnel, washed with 2–3 liters of acetic acid and then air dried.

PROCESS

Flow Reactor

Several modified resins are prepared as described above using sufficient modifier to exchange with about 4.5% of the sulfonic acid groups present on the unmodified resin. The resin utilized is Dowex MSC-1H of Dow Chemical Company.

The modified ion exchange resins and an unmodified resin are tested in a flow reactor as follows: acetic acid is first saturated with butadiene by passing acetic acid down through a packed saturator through which butadiene is passed in an upflow mode. Flow rates are adjusted to produce saturated acetic acid at the offtake at the bottom of the saturator. Liquid hourly space velocities of acetic acid of about 1 and gaseous hourly space velocities of butadiene of about 40 are used. The saturated acetic acid is then passed to a reactor which is jacketed and maintained at a temperature of about 50° C. Feed flow is in the upflow mode through the reactor, product is removed from the top of the reactor and appropriately analyzed by chromatographic means. The data for the selectivity to butenyl acetates has been normalized to a 50% butadiene conversion level and is shown in Table 1. As can be seen from the table, modifier resins produce high selectivities of around 90%.

TABLE 1

ACETOXYLATION OF BUTADIENE

| Modifier | Selectivity to Butenyl Acetates, mol. % |
|---|---|
| None | 62 |
| $C_5H_{11}{}^+N$  | 90 |
| $C_{12}H_{25}{}^+N$  | 92 |

Batch Reactor

The resin catalysts of the instant invention are also suitable for use in a batch reactor. In a typical batch reaction process a modified catalyst resin and acetic acid are added to a batch reactor. Reactor is then pressurized with butadiene heated to reaction temperature from about 50°–80° C. and maintained at this temperature for up to about 2 hours. After reaction, the reaction is cooled and the product worked up. The use of the modified ion exchange resins of the instant invention will be shown to have converted the reactants to butenyl acetates in high selectivity.

I claim:

1. A process for producing butenyl acetates which comprises reacting butadiene and acetic acid at a temperature ranging from about 0° to about 150° C. in the presence of a catalyst comprising styrene-divinylbenzene sulfonic acid ion exchange resin wherein from about 2 to about 20% of the sulfonic acid moieties of the resin are exchanged with an alkyl pyridinium salt.

2. The process of claim 1 wherein from about 3 to about 10% of the sulfonic acid moieties are exchanged.

3. The process of claim 1 or 2 where the alkyl moiety of the pyridinium salt has a carbon number from 1 to about 20.

4. The process of claim 1 or 2 wherein the alkyl pyridinium salt is a pentyl pyridinium or a dodecyl pyridinium salt.

* * * * *